US005792899A

United States Patent [19]
Cottrell

[11] Patent Number: 5,792,899
[45] Date of Patent: Aug. 11, 1998

[54] PROCESS FOR THE MANAGEMENT OF POLYNUCLEAR AROMATIC COMPOUNDS PRODUCED IN A HYDROCARBON DEHYDROGENATION REACTION ZONE

[75] Inventor: Paul R. Cottrell, Arlington Heights, Ill.

[73] Assignee: UOP LLC, Des Plaines, Ill.

[21] Appl. No.: 723,205

[22] Filed: Sep. 27, 1996

[51] Int. Cl.$^6$ ............................ C07C 7/12; C07C 41/00; C07C 1/00
[52] U.S. Cl. .................. 585/827; 585/319; 585/330; 585/655; 585/804; 585/809; 585/820; 568/697; 568/699
[58] Field of Search ..................... 585/655, 330, 585/319, 804, 809, 820, 827; 568/697, 699

[56] References Cited

U.S. PATENT DOCUMENTS

| | | | |
|---|---|---|---|
| 4,026,795 | 5/1977 | Okamoto et al. | 502/23 |
| 4,430,517 | 2/1984 | Imai et al. | 585/660 |
| 4,558,168 | 12/1985 | Gussow et al. | 585/809 |
| 5,276,231 | 1/1994 | Kocal et al. | 585/319 |
| 5,481,060 | 1/1996 | Scott et al. | 585/867 |

*Primary Examiner*—Glenn Caldarola
*Assistant Examiner*—In Suk Bullock
*Attorney, Agent, or Firm*—Thomas K. McBride; John G. Tolomei; John G. Cutts, Jr.

[57] ABSTRACT

A process for the management of polynuclear aromatic compounds produced in a hydrocarbon dehydrogenation zone wherein the effluent from the hydrocarbon dehydrogenation zone is contacted with an adsorbent to reduce the concentration of polynuclear aromatic compounds. The resulting dehydrogenated hydrocarbon having a reduced concentration of polynuclear aromatic compounds is reacted with methanol to produce an ether. A portion of the ether is contacted with a spent bed of adsorbent to recover at least a portion of the polynuclear aromatic compounds adsorbed thereon to thereby regenerate the adsorbent.

9 Claims, 1 Drawing Sheet

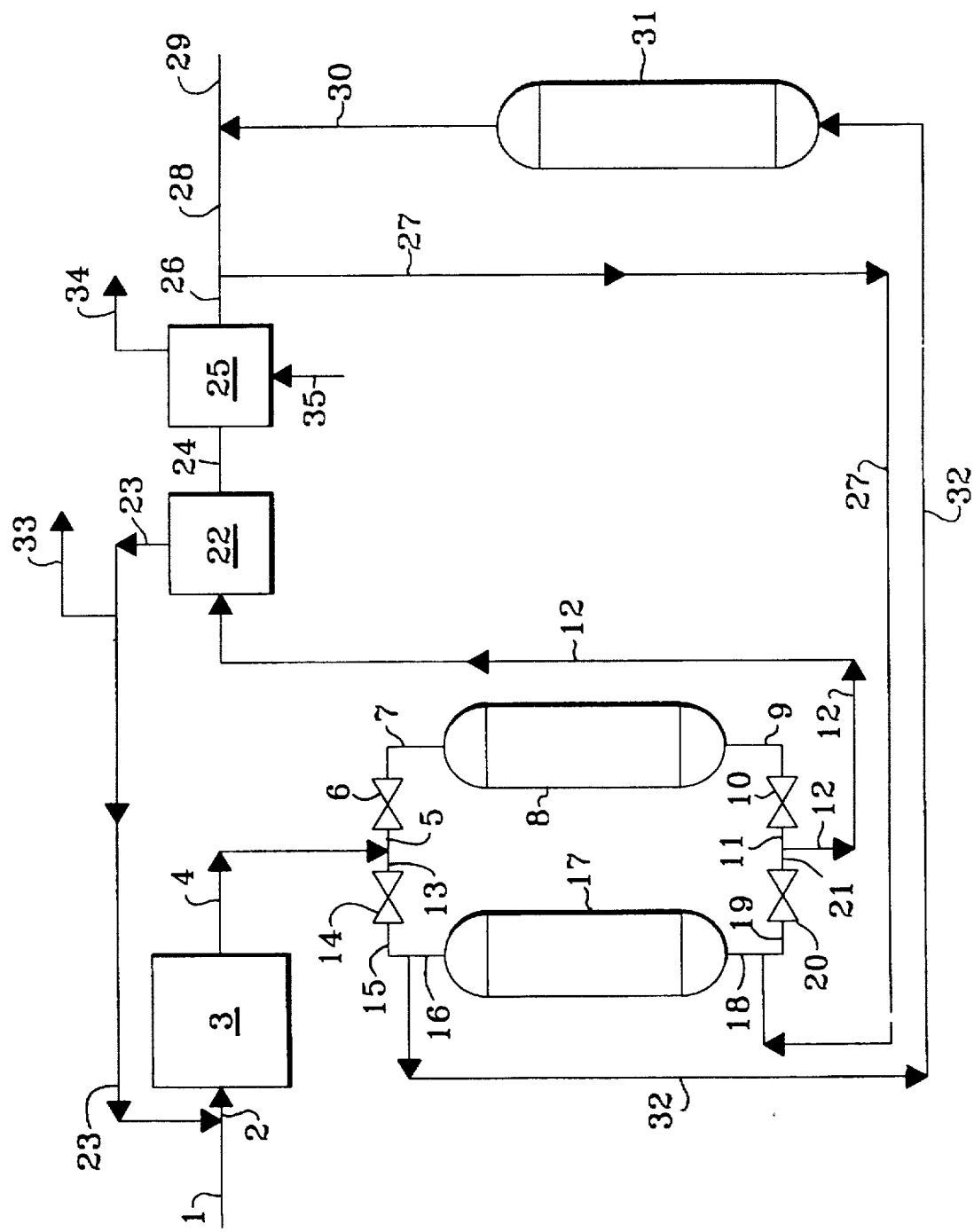

PROCESS FOR THE MANAGEMENT OF POLYNUCLEAR AROMATIC COMPOUNDS PRODUCED IN A HYDROCARBON DEHYDROGENATION REACTION ZONE

FIELD OF THE INVENTION

The field of art to which this invention pertains is the removal and recovery of polynuclear aromatic compound co-products from the vapor effluent from a normally gaseous hydrocarbon dehydrogenation reaction zone.

BACKGROUND OF THE INVENTION

A The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater operation severity of existing commercial facilities has highlighted the problem which occurs in the product recovery section of hydrocarbon dehydrogenation processes. This problem is the result of the production of trace quantities of polynuclear aromatic compounds. The polynuclear aromatic compounds are not only an undesired impurity, but also present a severe operational problem because when they condense and plate out on the cooler surfaces of the plant, there are detrimental results. The deposits of polynuclear aromatic compounds are difficult to remove, they reduce the efficiency of heat exchangers and they may eventually lead to plugging.

In the case where the dehydrogenated compounds are used in subsequent processes, a sudden surge of the polynuclear aromatic compounds into the dehydrogenation effluent can contaminate the resulting products from the subsequent processes. The presence of polynuclear aromatic compounds changes the color quality of products and the value or marketability of the products is significantly reduced.

Therefore, those skilled in the art of hydrocarbon processing have sought methods to overcome the problem posed by the production of polynuclear aromatic compounds in dehydrogenation production facilities. The process of the present invention provides a facile and economical solution to the problem of the production of polynuclear aromatic compounds in a dehydrogenation plant.

BRIEF SUMMARY OF THE INVENTION

The present invention relates to a process for the management of polynuclear aromatic compounds produced in a hydrocarbon dehydrogenation zone wherein the effluent from the hydrocarbon dehydrogenation reaction zone is contacted with an adsorbent to reduce the concentration of the polynuclear aromatic compound. The resulting dehydrogenated hydrocarbon having a reduced concentration of polynuclear aromatic compound is reacted with methanol to produce an ether. A portion of the ether is contacted with a spent bed of adsorbent to recover at least a portion of the polynuclear aromatic compound adsorbed thereon to thereby regenerate the adsorbent. In a preferred embodiment of the present invention, the ether is recovered by removing the polynuclear aromatic compound from the ether by contact with a separate adsorbent bed.

One embodiment of the present invention may be characterized as a process for the management of polynuclear aromatic compounds produced in a hydrocarbon dehydrogenation reaction zone which process comprises: (a) contacting the effluent from a hydrocarbon dehydrogenation reaction zone comprising dehydrogenated hydrocarbons, dehydrogenatable hydrocarbons and trace quantities of polynuclear aromatic compounds with a first adsorbent to reduce the water and polynuclear aromatic compounds concentrations of the effluent; (b) separating the resulting dried effluent from step (a) to produce a hydrocarbon stream comprising dehydrogenated hydrocarbons; (c) reacting at least a portion of the hydrocarbon stream comprising dehydrogenated hydrocarbons with methanol to produce a stream comprising an ether compound; and (d) contacting a second adsorbent comprising polynuclear aromatic compounds with at least a portion of the stream comprising an ether compound to recover at least a portion of the polynuclear aromatic compounds to thereby regenerate the second adsorbent.

Another embodiment of the present invention may be characterized as a process for the management of polynuclear aromatic compounds produced in a hydrocarbon dehydrogenation reaction zone which process comprises: (a) contacting the effluent from a hydrocarbon dehydrogenation reaction zone comprising dehydrogenated hydrocarbons, dehydrogenatable hydrocarbons and trace quantities of polynuclear aromatic compounds with a first adsorbent to reduce the water and polynuclear aromatic compounds concentrations of the effluent; (b) separating the resulting dried effluent from step (a) to produce a hydrocarbon stream comprising dehydrogenated hydrocarbons; (c) reacting at least a portion of the hydrocarbon stream comprising dehydrogenated hydrocarbons with methanol to produce a stream comprising an ether compound; (d) contacting a second adsorbent comprising polynuclear aromatic compounds with at least a portion of the stream comprising an ether compound to recover at least a portion of the polynuclear aromatic compounds to thereby regenerate the second adsorbent; and (e) contacting at least a portion of the resulting stream comprising an ether compound and dissolved polynuclear aromatic compounds from step (d) with a third adsorbent to produce a stream comprising an ether compound having a reduced concentration of dissolved polynuclear aromatic compounds.

Other embodiments of the present invention encompass further details such as preferred dehydrogenated hydrocarbons, adsorbents and operating conditions.

The process of the present invention provides the advantages of the ability to remove and isolate polynuclear aromatic compounds which are present in the effluent from a hydrocarbon dehydrogenation reaction zone. This management of polynuclear aromatic compounds greatly reduces the undesirable deposition of polynuclear aromatic compounds in the process plant and thereby greatly enhances the operability of the plant.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the removal and recovery of trace quantities of polynuclear aromatic compounds from the vapor effluent of a hydrocarbon dehydrogenation zone. The dehydrogenation of paraffinic hydrocarbons is well known to those skilled in the art of hydrocarbon processing.

In the dehydrogenation process, fresh hydrocarbon feed is combined with recycle hydrogen and recycled unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream containing olefinic hydrocarbons. In accordance with the present invention, the effluent from the catalytic dehydrogenation reaction zone contains unconverted saturated hydrocarbons, olefin hydrocarbons and polynuclear aromatic compounds in an amount from about 50 to about 500 wppm.

In accordance with the present invention, the dehydrogenation reaction zone effluent is preferably compressed and cooled to a temperature in the range from about 50° F. (10° C.) to about 200° F. (93° C.) and contacted with an adsorbent in an adsorption zone in order to separate and recover the trace quantities of polynuclear aromatic compounds which are contained in the dehydrogenation reaction zone effluent. preferred adsorbent is selected from the group consisting of activated alumina and molecular sieve.

The resulting effluent from the adsorption zone has a reduced concentration of polynuclear aromatic compounds and is further cooled to a temperature in the range from about 50° F. (10° C.) to about −120° F. (−84° C.) and introduced into a vapor-liquid separation zone to produce a high purity gaseous hydrogen stream and a liquid stream containing dehydrogenated hydrocarbons and dehydrogenatable hydrocarbons. This resulting liquid stream containing dehydrogenated hydrocarbons is introduced along with a methanol feed stream into an etherification zone wherein the methanol and the dehydrogenated hydrocarbons are reacted to produce the corresponding ether and a stream containing dehydrogenatable hydrocarbon which may be recycled to the dehydrogenation zone if desired.

A slipstream of the produced ether is introduced into an off-line adsorbent zone containing spent adsorbent which contains polynuclear aromatic compounds adsorbed thereon in order to solubilize and remove the polynuclear aromatic compounds and thereby regenerate the adsorbent. In a preferred embodiment of the present invention, the resulting ether stream containing dissolved polynuclear aromatic compounds is contacted with an adsorbent to finally recover the polynuclear aromatic compounds and to return the resulting clean ether stream to the etherification product stream. Any suitable adsorbent may be utilized to trap the polynuclear aromatic compounds and purify the ether. preferred adsorbents may be selected from the group consisting of activated carbon, activated alumina and molecular sieve.

In the event that the dehydrogenated hydrocarbon is isobutylene and is reacted with methanol, the resulting ether will be methyl tert butyl ether (MTBE).

DETAILED DESCRIPTION OF THE DRAWING

With reference now to the drawing, a normally gaseous dehydrogenatable hydrocarbon feedstock is introduced into the process via conduit 1 and is admixed with a recycle hydrogen stream provided via conduit 23 and the resulting admixture is introduced via conduit 2 into dehydrogenation zone 3. A resulting effluent from dehydrogenation zone 3 containing dehydrogenated hydrocarbons, dehydrogenatable hydrocarbons and trace quantities of polynuclear aromatic compounds is transported via conduit 4, conduit 5, valve 6 and conduit 7 and introduced into adsorbent zone 8. A resulting hydrocarbon stream containing a reduced level of water and polynuclear aromatic compounds is removed from adsorption zone 8 and transported via conduit 9, valve 10, conduit 11 and conduit 12, and is introduced into vapor-liquid separation zone 22. A hydrogen-rich gaseous stream is removed from vapor-liquid separation zone 22 via conduit 23 and recycled as described hereinabove. A net hydrogen gas stream is removed via conduit 33. A liquid hydrocarbon stream containing dehydrogenated hydrocarbons and dehydrogenatable hydrocarbons is removed from vapor-liquid separation zone 22 via conduit 24 and introduced into etherification zone 25. Methanol is introduced via conduit 35 into etherification zone 25. A resulting ether stream is removed from etherification zone 25 and transported and recovered via conduits 26, 28 and 29. A resulting stream containing dehydrogenatable hydrocarbons is removed from etherification zone 25 via conduit 34. A slipstream of ether produced in etherification zone 25 is transported via conduits 26, 27 and 18 and is introduced into adsorption zone 17. A resulting ether stream containing dissolved polynuclear aromatic compounds is removed from adsorption zone 17 via conduits 16 and 32 and introduced into adsorption zone 31. A clean ether stream is removed from adsorption zone 31 via conduits 30 and 29 and recovered. Conduits 13 and 15, in conjunction with valve 14, and conduits 19 and 21, in conjunction with valve 20, are utilized when adsorption zone 17 is put on-line to replace adsorption zone 8 during its regeneration.

ILLUSTRATIVE EMBODIMENT

An isobutane feed stream in an amount of 250,000 mass units per hour was introduced into a dehydrogenation zone to convert 42 weight percent of the feed to isobutylene. Recycle hydrogen is also introduced into the dehydrogenation zone in an amount of 100,000 standard cubic feet per hour. The resulting effluent from the dehydrogenation zone contains 77 ppm polynuclear aromatic compounds based on hydrocarbon and is introduced in an adsorption zone containing activated alumina to reduce the level of polynuclear aromatic compounds to less than 1 ppm. The resulting effluent from the adsorption zone is compressed and cooled to a temperature of −120° F. (−84° C.) which is subsequently introduced into a vapor-liquid separation zone to produce a hydrogen-rich gaseous stream which is recycled to the dehydrogenation zone and a liquid hydrocarbon stream containing isobutane and isobutylene.

The liquid hydrocarbon stream containing isobutane and isobutylene is introduced into an etherification zone along with a feed stream of methanol and reacted across an acidic resin catalyst system to produce a stream containing methyl tert butyl ether (MTBE) in an amount of 166,000 mass units per hour. Another hydrocarbon stream containing 75,000 mass units per hour of isobutane is recovered from the etherification zone. A slipstream of the product MTBE in an amount of 10,000 mass units per hour is introduced into a spent, off-line adsorption zone containing an activated alumina with adsorbed polynuclear aromatic compounds in order to regenerate the adsorption zone and dissolve the polynuclear aromatic compounds in the MTBE. The resulting MTBE containing dissolved polynuclear aromatic compounds is then contacted with activated carbon in the adsorption zone to deposit the polynuclear aromatic compounds thereon and produce an MTBE suitable as a final product.

The foregoing description and illustrative embodiment clearly illustrate the advantages encompassed by the method of the present invention and the benefits to be afforded with the use thereof.

What is claimed:

1. A process for the management of polynuclear aromatic compounds produced in a hydrocarbon dehydrogenation reaction zone which process comprises:
   (a) contacting the effluent from a hydrocarbon dehydrogenation reaction zone comprising dehydrogenated hydrocarbons, dehydrogenatable hydrocarbons and trace quantities of polynuclear aromatic compounds with an adsorbent to reduce the water and polynuclear aromatic compounds concentrations of said effluent;
   (b) separating the resulting dried effluent from step (a) to produce a hydrocarbon stream comprising dehydrogenated hydrocarbons;
   (c) reacting at least a portion of said hydrocarbon stream comprising dehydrogenated hydrocarbons with methanol to produce a stream comprising an ether compound; and
   (d) contacting said adsorbent comprising polynuclear aromatic compounds with at least a portion of said stream comprising an ether compound to recover at least a portion of said polynuclear aromatic compounds to thereby regenerate said adsorbent.

2. The process of claim 1 wherein the resulting stream comprising an ether compound and dissolved polynuclear aromatic compounds from step (d) is contacted with an adsorbent to produce a stream comprising an ether compound having a reduced concentration of dissolved polynuclear aromatic compounds.

3. The process of claim 1 wherein said dehydrogenated hydrocarbons are selected from the group consisting of ethylene, propylene and butylene.

4. The process of claim 1 wherein said polynuclear aromatic compounds are present in the effluent from a hydrocarbon dehydrogenation reaction zone in an amount from about 50 to about 500 wppm.

5. The process of claim 1 wherein said ether compound is methyl tert butyl ether.

6. The process of claim 1 wherein step (a) is conducted at a temperature from about 50° F. (10° C.) to about 200° F. (93° C.).

7. The process of claim 1 wherein said adsorbent is selected from the group consisting of activated alumina and molecular sieve.

8. The process of claim 2 wherein said adsorbent is selected from the group consisting of activated carbon, activated alumina and molecular sieve.

9. A process for the management of polynuclear aromatic compounds produced in a hydrocarbon dehydrogenation reaction zone which process comprises:
   (a) contacting the effluent from a hydrocarbon dehydrogenation reaction zone comprising dehydrogenated hydrocarbons, dehydrogenatable hydrocarbons and trace quantities of polynuclear aromatic compounds with a first adsorbent to reduce the water and polynuclear aromatic compounds concentrations of said effluent;
   (b) separating the resulting dried effluent from step (a) to produce a hydrocarbon stream comprising dehydrogenated hydrocarbons;
   (c) reacting at least a portion of said hydrocarbon stream comprising dehydrogenated hydrocarbons with methanol to produce a stream comprising an ether compound;
   (d) contacting the first adsorbent comprising polynuclear aromatic compounds with at least a portion of said stream comprising an ether compound to recover at least a portion of said polynuclear aromatic compounds to thereby regenerate said adsorbent; and
   (e) contacting at least a portion of the resulting stream comprising an ether compound and dissolved polynuclear aromatic compounds from step (d) with a second adsorbent to produce a stream comprising an ether compound having a reduced concentration of dissolved polynuclear aromatic compounds.

* * * * *